United States Patent [19]

Swedo et al.

[11] 4,197,393
[45] Apr. 8, 1980

[54] BIPHENYLENE POLYMERS AND RESINS AND THE PRODUCTION THEREOF

[75] Inventors: Raymond J. Swedo; Carl S. Marvel, both of Tucson, Ariz.

[73] Assignee: University Patents, Inc., Norwalk, Conn.

[21] Appl. No.: 910,423

[22] Filed: May 30, 1978

[51] Int. Cl.² ................. C08G 63/66; C08G 63/68
[52] U.S. Cl. .................... 528/173; 528/179; 528/180; 528/190; 528/193; 528/194
[58] Field of Search ............ 528/180, 173, 190, 194, 528/193, 179

[56] References Cited
U.S. PATENT DOCUMENTS

| 3,725,070 | 4/1973 | Hamb et al. | 528/190 |
| 3,859,254 | 1/1975 | Hamb et al. | 528/190 |

Primary Examiner—Lester L. Lee
Attorney, Agent, or Firm—Mason, Kolehmainen, Rathburn & Wyss

[57] ABSTRACT

Polymers of the following formulas, and cross-linked resins formed therefrom through thermal cleavage of the four-membered rings of the biphenylene nuclei, are useful as molding and laminating materials:

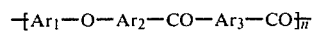
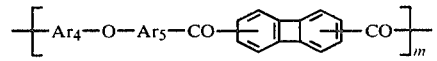

and
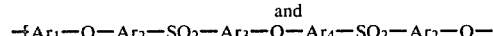
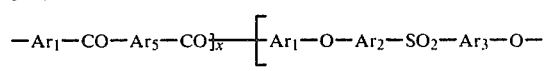
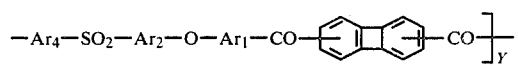

wherein $Ar_1$, $Ar_2$, $Ar_3$, $Ar_4$ and $Ar_5$ are the same or different bivalent aromatic hydrocarbon radicals containing six to ten carbons, n is an integer from 100 to 200, m is an integer from 5 to 25, x is an integer from 50 to 100, and y is an integer from 3 to 12. In the preferred modifications, n is an integer from 50 to 190 and m is an integer from 8 to 15, and the preferred ratio of n to m is from about 18:1 to about 20:1; in one species n is about 152 and m is about 8, while in a related species n is about 190 and m is about 10. In the other preferred modifications, x is an integer from 55 to 75 and y is an integer from 6 to 9, and the preferred ratio of x to y is from about 8:1 to about 10:1; in one species x is about 60 and y is about 7, while in a related species x is about 72 and y is about 8.

25 Claims, 8 Drawing Figures

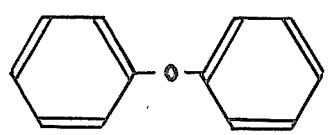
I
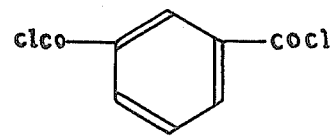
II
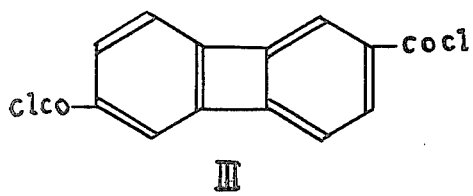
III
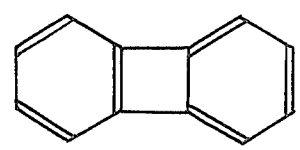
IV
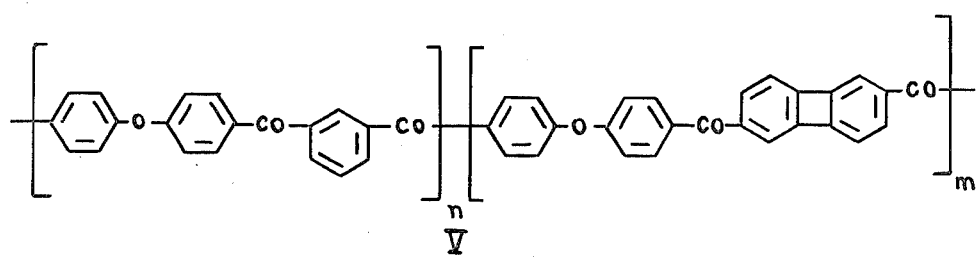
V
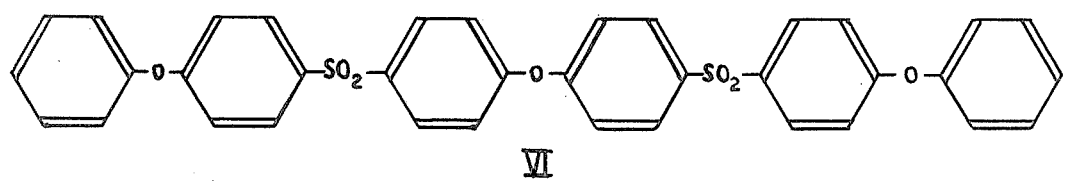
VI
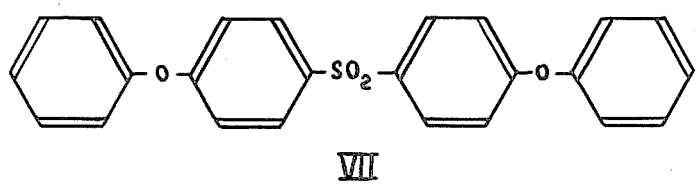
VII

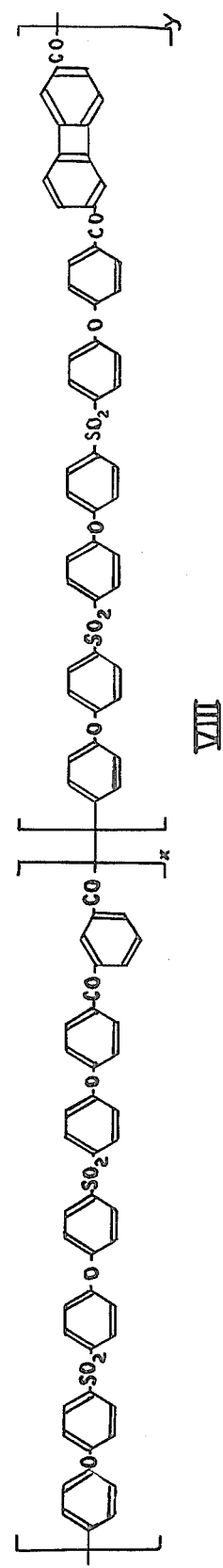

BIPHENYLENE POLYMERS AND RESINS AND THE PRODUCTION THEREOF

This invention relates to organic polymers containing biphenylene nuclei and to cross-linked forms of such polymers. The invention also relates to methods of producing such polymers.

BACKGROUND OF THE INVENTION

Filled resins, e.g., glass fiber and fabric reinforced resins, are well known as suitable materials for forming structural units in the aircraft and other industries. A wide variety of resins have been proposed in the past for formulating such structures and as laminating resins for joining various materials. For example, polyester, epoxy and polycarbonate resins have been utilized as matrix resins for glass fiber-resin laminates. One of the difficulties experienced in the use of these resins, however, is that they are difficult to mold and mechanically work. Thus, it is often necessary to apply the resin in liquid form to the glass fibers on substrate to be laminated and then solidify the composite in order to obtain a suitable product. The resins previously used have to be melted or dissolved in a suitable solvent in order to achieve the desired liquid form. Many of these resins, however, decompose or suffer some deleterious chemical change when heated to temperatures sufficiently high to achieve melting. The result is a laminate or reinforced resin with reduced strength and physical properties.

In addition, the prior art matrix and laminating resins do not possess a sufficiently high degree of thermal stability which is requisite in many industrial applications.

It has been heretofore proposed to provide low-melting laminating polymers. These polymers may be melted at low temperatures, contacted with the filler material or substrate to be laminated and cured or cross-linked to the resinous state. A serious disadvantage associated with these low-melting polymers, however, is that cross-linking involves a chemical reaction which liberates a volatile by-product such as carbon dioxide or water. The liberation of these reaction products operates to form voids in the resulting product. Obviously, the prior art low-melting laminating polymers may not be used in applications requiring close tolerance or uniform compositions throughout.

It is an object of the invention to provide relatively low-melting polymers which may easily be admixed with fillers or contacted with substrates to be laminated and then cross-linked to form a firmly bonded article having a uniform composition throughout.

It is a further object of the invention to provide novel reinforced and laminated resin compositions having high degrees of strength and thermal stability.

It is another object to provide low-melting polymers which may be cross-linked without the production of volatile materials.

Another object is to provide infusible cross-linked resins.

SUMMARY OF THE INVENTION

The above and other objects are achieved by providing relatively low-melting polymers containing biphenylene nuclei or units. These polymers are produced from a diaryl ether such as diphenyl ether or a polyaryl ether sulfone, such as 1,3-bis(p-phenoxybenzenesulfonyl)benzene or 4,4'-bis(p-phenoxybenzenesulfonyl)diphenyl ether, by Friedel-Crafts polymerization with isophthaloyl or terephthaloyl chloride and a biphenylenedicarboxylic acid dichloride. The dibasic acid chlorides link the diaryl ether and polyaryl ether sulfone molecules together in substantially linear polymers with molecular weights from about 30,000 to about 100,000. The polymers so produced are relatively low-melting and are suitable for laminations. They are readily cured or cross-linked by heating at relatively low temperature to produce strong infusible resins. The cross-linking occurs by thermal cleavage of the four-membered ring of the biphenylene nucleus. The cross-linking takes place without the release of void-forming volatile materials.

When the biphenylene polymers of this invention are cross-linked while in contact with a filler or substrate to be laminated, the result is a product having a high degree of strength and thermal stability wherein the cross-linked polymer is firmly adhered to the filler or substrate.

BRIEF DESCRIPTION OF THE DRAWING

Reference is made to the attached drawing (two sheets) which illustrates by structural formula the starting materials and some of the polymers of this invention. In the drawing, IV represents the biphenylene nucleus or unit which provides crosslinking of the polymers, and III represents biphenylene-2,6-dicarboxylic acid chloride which is a starting material for the polymers of this invention. Formula II illustrates isophthaloyl chloride, which with III, provides the acid chlorides which react with diphenyl ether (I) and produce polymers of the type illustrated by V. In V, n is an integer from about 100 to 200 and m is an integer from about 5 to 25.

In the drawing, VI illustrates 4,4'-bis(p-phenoxybenzenesulfonyl)diphenyl ether and VII illustrates 4,4'-diphenoxydiphenyl sulfone, which can also be components in the polymers. Either may replace all or part of the diphenyl ether (I) in the polymers.

The general formula VIII represents a polymer produced from VI (in lieu of I) with isophthaloyl chloride (II) and biphenylene-2,6-dicarboxylic acid chloride (III). In VIII, X is an integer from about 50 to 100 and y is an integer from about 3 to 12. An analogous polymer can be produced by using VII in lieu of VI, in reaction with II and III.

GENERAL DESCRIPTION OF THE INVENTION

The polymers illustrated by V and VIII are linear polymers made from two acid chlorides (II and III) and one of the aromatic ethers (I, VI and VII), by Friedel-Crafts polymerization. Terephthaloyl chloride can be used in lieu of II to produce similar polymers. Other position isomers of III are also useful in producing such polymers. In practice about 20 moles of the isophthaloyl or terephthaloyl chloride are used for each mole of biphenylenedicarboxylic acid chloride, but the amount can vary from 5 moles to 30 moles of the former to one mole of the latter.

Similar polymers can be produced by replacing part of the diphenyl ether (I) in V by one or both of the more complex ethers VI or VII. When I is replaced completely by VI, the resulting polymer is that illustrated by VIII. This polymer is more soluble in organic solvents than is V.

In the drawing the sequence of components in V and VIII is illustrated as regular or uniform, but in practice the sequence is random. For example, another form of polymer V can be represented as

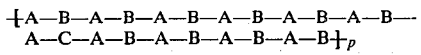

where A represents the diphenyl ether nucleus —C₆H₄—O—C₆H₄— B represents the isophthaloyl or terephthaloyl nucleus

C represents the biphenylenedicarboxyl nucleus —CO—C₁₂H₆—CO which is derived from III by loss of the chlorine atoms, and p is an integer from about 10 to 20.

In a similar way, another form of polymer VIII can be represented as

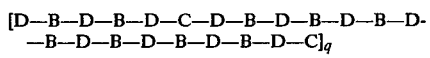

where D represents a bivalent radical of VI, B and C have the meanings given above, and q is integer from about 10 to 15.

It is apparent that each of the polymers V and VIII can be illustrated in a variety of random sequences of the moieties represented by A, B, C and D. In addition, other polymer components such as VII can be substituted for all or part of I or VI, thus making the random sequence even more complex.

The polymerization is conducted under Friedel-Crafts conditions with a Friedel-Crafts catalyst, preferably anhydrous aluminum chloride in a inert solvent such as dichloroethane, chloroform or the like under anhydrous conditions.

The linear polymers are quite stable. They soften between 150° and 300° C. and melt at higher temperatures. They are converted at high temperature to cross-linked resins as described below. Some are moderately soluble in organic solvents while others are quite insoluble in all common solvents. They adhere well to glass fibers and act as laminating plastics.

The linear polymer made from 25 moles of diphenyl ether, 23.75 moles of isophthaloyl chloride and 1.25 mole of biphenylene-2,6-dicarboxylic acid chloride with anhydrous aluminum chloride at room temperature was obtained in essentially quantitative yield. It had a softening point of 240° C. and melted to a clear liquid at 270° C. It was not soluble in any common organic solvent but did dissolve in concentrated sulfuric acid and had an inherent viscosity of 0.53 (0.1250 g in 25 ml H₂SO₄) at 30° C. When heated to 305° C. for 20 hours, it cured to an insoluble resin which had a Vicat softening point of 460°–500° C. This cured resin lost only 0.9% of its weight on isothermal aging at 300° C. in circulating air and only a further 1% of its weight after another 24 hours of heating at 350° C.

The uncured polymer when melted on a glass mat gave a good laminate which did not become brittle even when cooled in dry ice.

CROSSLINKED RESINS

Linear polymers of the types illustrated by V and VIII, or any modifications thereof of the types described above, can be crosslinked by heating at high temperature, usually above the melting points of the polymers (for instance, at 300°–350° C.). The heating causes thermal cleavage of the four-membered ring of the biphenylene nucleus, thus creating a biradical (a bivalent free radical) which can form linkages with similar free radicals in adjacent polymers, thus cross-linking the polymers. These biphenylene polymers can be cross-linked without the formation of volatile by-products. The resultant cross-linked materials are high-melting resins which are useful as laminating bonding or reinforcing resins for glass, metals, plastics and other materials. These crosslinked materials are infusible, insoluble resins of great stability to heat, air and sunlight.

The invention is disclosed in more detail by the following examples which describe the preparation and properties of certain linear polymers and crosslinked resins within the scope of the general description. These examples are only illustrative of the various polymers and resins that can be produced in accordance with this specification. It will be understood that numerous changes in starting materials, operating conditions and the like, may be made within the description set forth in this specification.

EXAMPLE 1

Biphenylene-2,6-dicarboxylic acid

Chlorine was passed into an ice-cooled solution of 42.5 g of sodium hydroxide in 425 ml of water until 29.65 g of the gas had been absorbed. A 268 ml portion of this solution was added to a mixture of 3.95 g of 2,6-diacetylbiphenylene in 340 ml of 1,4-dioxane, heated in a bath maintained at 75° C. The temperature of the bath was then increased to 95° C., and heating was continued. After one hour, an additional 133 ml of the hypochlorite solution was added, and heating and stirring at 95° C. were continued for an additional 12 hours. The mixture was then concentrated under reduced pressure to remove the dioxane, and the solution was filtered; the filtrate was retained. The solid was taken up in water to dissolve the diacid salt, and the solution was again filtered. The filtrates were combined, treated with sodium bisulfite, acidified with dilute hydrochloric acid, and the precipitated biphenylene-2,6-dicarboxylic acid was filtered, washed with water, and dried under vacuum. The yield of the diacid was 3.75 g (92% yield), mp 350° C. with decomposition. Reprecipitation of the diacid from aqueous sodium hydroxide or ammonium hydroxide solutions with dilute hydrochloric acid produced no change in the product. Treatment of the product with hot, concentrated hydrochloric acid also resulted in no change. Although the diacid prepared by this procedure contained some acid salt, it was sufficiently pure to use for the preparation of the diacid chloride.

EXAMPLE 2

Biphenylene-2,6-dicarboxylic acid chloride

Biphenylene-2,6-dicarboxylic acid (3.68 g) was refluxed with 175 ml of thionyl chloride for 16 hours. Upon cooling, crystals of the diacid chloride separated. These were filtered, washed with cold thionyl chloride, and dried. Recrystallization from xylene gave 3.71 g of biphenylene-2,6-dicarboxylic acid chloride (87% yield), mp 242°–244° C.

EXAMPLE 3

Condensation of Diphenyl ether with Isophthaloyl chloride and Biphenylene-2,6-dicarboxylic acid chloride Diphenyl ether (4.25 g, 25.0 mmol), isophthaloyl chloride (4.82 g, 23.75 mmol), and biphenylene-2,6-dicarboxylic acid chloride (0.35 g, 1.25 mmol, 5 mole % based on diphenyl ether) were dissolved in 200 ml of 1,2-dichloroethane. Anhydrous aluminum chloride (8.5 g, 64 mmol) was added, and the mixture was stirred under $N_2$ at room temperature. Polymer began to precipitate after 20 minutes. After 20 hours, the polymer was filtered and washed with water to remove aluminum chloride. The solid was washed three times with methanol in a blender, and dried under vacuum to yield 7.2 g of polymer (92% yield), softening point 240°–270° C. The polymer was completely soluble in $H_2SO_4$ and had an inherent viscosity ($\eta_{inh}$) of 0.53 in $H_2SO_4$ at 30° C. (0.1250 g in 25 ml $H_2SO_4$).

EXAMPLE 4

Example 3 was repeated with 27.38 g of diphenyl ether, 30.95 g of isophthaloyl chloride, 2.22 g of biphenylene-2,6-dicarboxylic acid chloride, 54.75 g of anhydrous aluminum chloride and 1300 ml of 1,2-dichloroethane. There was produced 47.2 g of polymer (94% yield) with the same mp as obtained in Example 3.

EXAMPLE 5

Crosslinking of the Polymer

The polymer of Example 4 was successfully crosslinked by heating at 305° C. under $N_2$ for 20 hours. The crosslinked polymer showed insolubility in $H_2SO_4$, and had a Vicat softening range of 460°–500° C. Isothermal analysis in an aircirculating oven at 300° C. for three days resulted in a 0.9% weight loss; one additional day at 350° C. resulted in a further 1% loss of weight.

A sample of the original polymer cured at 305° C. for ¾ hour had the same appearance as the material cured for 20 hours, but a Vicat determinaton of this material showed less crosslinking than the 20-hour sample.

The original polymer was made into a glass fiber laminate which showed good flexibility, even when cooled in dry ice.

EXAMPLE 6

Condensation of 4,4′-Bis(p-phenyoxybenzenesulfonyl)diphenyl ether with Isophthaloyl dichloride and Biphenylene-2,6-dicarboxylic acid chloride 4,4′-Bis(p-phenoxybenzenesulfonyl)diphenyl ether (9.52 g; 15.0 mmole), isophthaloyl dichloride (2.74 g; 13.5 mmole), and biphenylene-2,6-dicarboxylic acid chloride (0.416 g; 1.5 mmole) were dissolved in 225 ml of dry 1,2-dichloroethane. The system was placed under argon, and anhydrous aluminum chloride (14.40 g, 108 mmole) was added with stirring. After 18 hours at room temperature, the polymer was filtered and washed successively in a blender with several portions each of water and methanol, filtering between each washing. The polymer was dried at 110° C./4 hr. under vacuum to yield 9.4 g of polymer (90%); mp = 240°–248° C.

The polymer is soluble in dimethylformamide, dimethylacetamide, and dimethyl sulfoxide, and had $\eta_{inh}$ =0.64 (0.1250 g polymer/25.00 ml conc. $H_2SO_4$, 30° C.). Vicat softening of this polymer (powder; 44.9 psi; $\Delta T=1°$ C./min.) showed sharp softening in the 150°–170° C. range. After curing at 330° C., under argon for one week, only a small, gradual softening in the 160°–250° C. range was observed.

EXAMPLE 7

Example 6 was repeated with more solvent. The polymer was made from 224 mmole diphenyl ether, 213 mmole isophthaloyl dichloride, and 11 mmole (5% based on diphenyl ether) biphenylene-2,6-dicarboxylic acid chloride, in 1850 ml 1,2-dichloroethane solvent, with 575 mmole anhydrous aluminum chloride catalyst, under an argon atmosphere. It had mp: 245°–270° C., and $\eta_{inh}$=0.40 (0.1250 g/25.00 ml conc. $H_2SO_4$ at 30° C.).

EXAMPLE 8

The polymer of Example 6 was molded and cured as follows:

The molding temperature was 581° F. (about 300° C.) and the pressure was about 20000 lb/sq. in. The mold was held at the top temperature and pressure for 1 hour and then allowed to cool but held under pressure for 20 hours. The I beam was then tested for tensile strength. Five moldings were made. The tensile strengths varied from 8276 psi to 11,395 psi with the average being 10,019 psi. The elongations varied from 3.2 to 4.5% with an average of 3.9%.

We claim:

1. A linear polymer biphenylene polymer consisting essentially of one of the general formulae

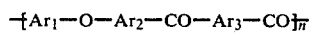

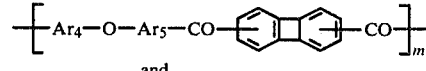

and

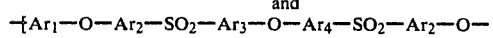

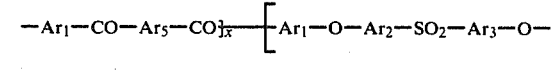

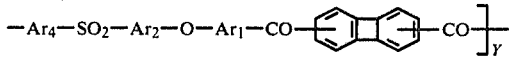

wherein $Ar_1$, $Ar_2$, $Ar_3$, $Ar_4$ and $Ar_5$ are the same or different bivalent aromatic hydrocarbon radicals containing six to ten carbons, n is an integer from 100 to 200, m is an integer from 5 to 25, x is an integer from 50 to 100, and y is an integer from 3 to 12.

2. A polymer according to claim 1 of the formula

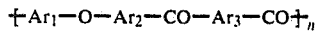

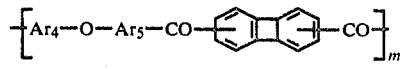

wherein $Ar_1$, $Ar_2$, $Ar_3$, $Ar_4$ and $Ar_5$ are the same or different bivalent aromatic hydrocarbon radicals containing six to ten carbons, n is a integer from 100 to 200 and m is an integer from 5 to 25.

3. A polymer according to claim 2 wherein $Ar_1$, $Ar_2$, $Ar_3$, $Ar_4$ and $Ar_5$ contain six carbon atoms.

4. A polymer according to claim 3 wherein n is an integer from 150 to 190 and m is an integer from 8 to 15.

5. A polymer according to claim 4 wherein the ratio of n to m is about 18:1 to 20:1.

6. A polymer according to claim 5 wherein n is about 152 and m is about 8.

7. A polymer according to claim 6 wherein n is about 190 and m is about 10.

8. A polymer according to claim 1 of the formula $$\left[Ar_1-O-Ar_2-SO_2-Ar_3-O-Ar_4-SO_2-Ar_2-O-Ar_1-CO-Ar_5-CO\right]_x\left[Ar_1-O-Ar_2-SO_2-Ar_3-O-Ar_4-SO_2-Ar_2-O-Ar_1-CO-\underset{\text{(biphenylene)}}{\bigodot}-CO\right]_y$$

wherein $Ar_1$, $Ar_2$, $Ar_3$, $Ar_4$, and $Ar_5$ are the same or different bivalent aromatic hydrocarbon radicals containing six to ten carbon atoms, x is an integer from 50 to 100, and y is an integer from 3 to 12.

9. A polymer according to claim 8 wherein $Ar_1$, $Ar_2$, $Ar_3$, $Ar_4$, and $Ar_5$ contain six carbon atoms.

10. A polymer according to claim 9 wherein x is an integer from 55 to 75 and y is an integer from 6 to 9.

11. A polymer according to claim 10 wherein the ratio of x to y is about 8:1 to 10:1.

12. A polymer according to claim 11 wherein x is about 60 and y is about 7.

13. A polymer according to claim 12 wherein x is about 72 and y is about 8.

14. Method of producing a polymer as defined by claim 2 where comprises:

(a) reacting a diaryl ether of the formula $$Ar_1-O-Ar_2$$

wherein $Ar_1$ and $Ar_2$ are the same or different bivalent aromatic hydrocarbon radicals containing six to ten carbon atoms, with a mixture of acid halides of the formulas $$X-CO-AR_3-CO-X$$

and $$X-CO-\underset{\text{(biphenylene)}}{\bigodot}-CO-X$$

wherein X is chlorine or bromine and $Ar_3$ is a bivalent aromatic hydrocarbon radical containing six to ten carbon atoms, in an inert organic solvent containing anhydrous aluminum chloride, and (b) removing the polymer so formed from the reaction mixture.

15. Method of claim 14 wherein $Ar_1$, $Ar_2$ and $Ar_3$ contain six carbon atoms and X is chlorine.

16. Method of claim 15 wherein the organic solvent is a halogenated alkane.

17. Method of claim 16 wherein the organic solvent is dichloroethane.

18. Method of producing a polymer as defined by claim 8 which comprises:

(a) reacting a diaryl ether of the formula $$Ar_1-O-Ar_2-SO_2-Ar_3-O-Ar_4-SO_2-Ar_2-O-Ar_1$$

wherein $Ar_1$, $Ar_2$, $Ar_3$ and $Ar_4$ are the same or different bivalent aromatic hydrocarbon radicals containing six to ten carbon atoms, with a mixture of acid halides of the formulas $$X-CO-Ar_5-CO-X$$

and $$X-CO-\underset{\text{(biphenylene)}}{\bigodot}-CO-X$$

wherein X is chlorine or bromine and $AR_5$ is a bivalent aromatic hydrocarbon radical containing six to ten carbon atoms, in an inert organic solvent containing anhydrous aluminum chloride, and (b) removing the polymer so formed from the reaction mixture.

19. Method of claim 18 wherein $Ar_1$, $Ar_2$ and $Ar_3$ contain six carbon atoms and X is chlorine.

20. Method of claim 19 wherein the organic solvent is a halogenated alkane.

21. Method of claim 20 wherein the organic solvent is dichloroethane.

22. Method of crosslinking a polymer defined by claim 1 which comprises heating said polymer at a temperature above the melting point of said polymers.

23. Method of claim 22 wherein the polymer is heated to a temperature in the range from 300° to 350° C.

24. A crosslinked resin produced by heating a polymer as defined by claim 1 to a temperature above the melting point of said polymer.

25. A crosslinked resin as set forth in claim 24 produced by heating the polymer to a temperature in the range from 300° to 350° C.

* * * * *